United States Patent [19]

Beriger et al.

[11] 4,262,012
[45] Apr. 14, 1981

[54] O-METHYL/ETHYL-S-PROPYL/BUTYL-O-PHENYL THIOPHOSPHATES AND DITHIOPHOSPHATES HAVING AN S-HETEROCYCLIC GROUP ON THE PHENYL RING

[75] Inventors: Ernst Beriger, Allschwil, Switzerland; Manfred Böger, Weil am Rhein, Fed. Rep. of Germany; Jozef Drabek, Allschwil; Odd Kristiansen, Möhlin, both of Switzerland

[73] Assignee: Ciba-Geigy Corporation, Ardsley, N.Y.

[21] Appl. No.: 751,918

[22] Filed: Dec. 17, 1976

Related U.S. Application Data

[60] Continuation-in-part of Ser. No. 534,934, Dec. 20, 1974, abandoned, which is a division of Ser. No. 408,874, Oct. 23, 1973, Pat. No. 3,898,305.

[30] Foreign Application Priority Data

Nov. 3, 1972 [CH] Switzerland .................. 16043/72
Nov. 4, 1973 [CH] Switzerland .................. 13638/73

[51] Int. Cl.³ .............. A61K 31/385; A61K 31/39; C07D 327/04; C07D 339/08
[52] U.S. Cl. .................. 424/276; 424/277; 549/22; 549/30; 549/35
[58] Field of Search ............ 260/327 M; 424/276, 424/277; 549/22, 30, 35

[56] References Cited

U.S. PATENT DOCUMENTS

| | | | |
|---|---|---|---|
| 3,247,223 | 4/1966 | Walsh et al. | 260/327 |
| 3,317,561 | 5/1967 | Levy et al. | 260/327 |
| 3,898,305 | 8/1975 | Beriger et al. | 549/30 X |

OTHER PUBLICATIONS

Cited to show maturation of parent Ser. No. 408,874 to U.S. Pat. 3,898,305 and lack of overlap of claims.

DT 68-793232, Derwent Belgian Patent Reports, vol. R, No. 8, p. 2, sec. No. 5, issued 4-2-70.

Primary Examiner—John D. Randolph
Attorney, Agent, or Firm—Frederick H. Rabin

[57] ABSTRACT

The invention relates to O,S-dialkyl-O-phenyl-thiophosphates and dithiophosphates of the formula

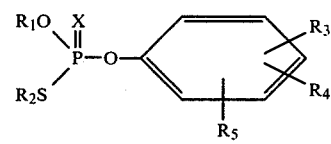

wherein
$R_1$ represents methyl or ethyl,
$R_2$ represents n-propyl, i-butyl or sec.-butyl,
$R_3$ and $R_4$ each represents hydrogen, chlorine, bromine, methyl or ethyl,
$R_5$ represents a group of the formula

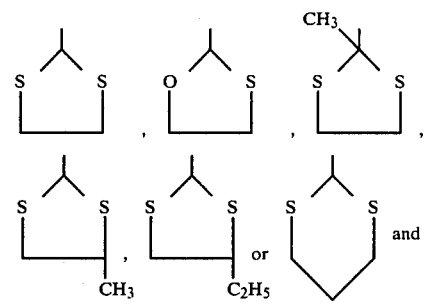

X represents oxygen or sulfur, which compounds possess useful pesticidal, in particular acaricidal and insecticidal properties.

16 Claims, No Drawings

O-METHYL/ETHYL-S-PROPYL/BUTYL-O-PHENYL THIOPHOSPHATES AND DITHIOPHOSPHATES HAVING AN S-HETEROCYCLIC GROUP ON THE PHENYL RING

CROSS REFERENCE

This application is a continuation-in-part of our application Ser. No. 534,934 filed on Dec. 20, 1974, now abandoned, which in turn was a divisional of our application Ser. No. 408,874 filed on Oct. 23, 1973, now U.S. Pat. No. 3,898,305.

DETAILED DISCLOSURE

The present invention relates to novel O,S-dialkyl-O-phenyl-thiophosphates and dithiophosphates having valuable pesticidal properties.

More particularly the present invention relates to the O,S-dialkyl-O-phenyl-thiophosphates and dithiophosphates of the formula I

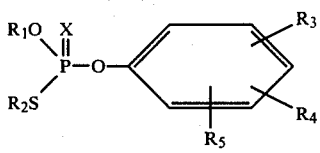

wherein
$R_1$ represents methyl or ethyl,
$R_2$ represents n-propyl, i-butyl or sec.-butyl,
$R_3$ and $R_4$ each represents hydrogen, chlorine, bromine, methyl or ethyl,
$R_5$ represents a group of the formula

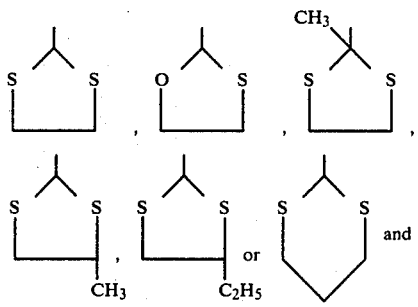

X represents oxygen or sulfur.

Compounds of the formula I which, on account of their pesticidal, in particular their insecticidal properties, are preferred are those of the formula I above wherein $R_2$ represents an n-propyl or sec.-butyl group and wherein X represents an oxygen atom.

The compounds of the formula I may be prepared by methods which are in themselves known, for example in accordance with the following reaction schemes:

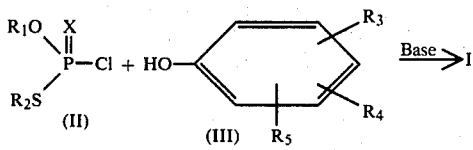

-continued

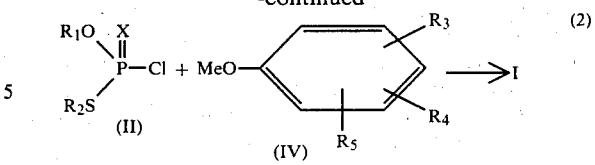

In the formulae II through Iv the symbols $R_1$ to $R_5$ and X have the meanings given above for formula I and Me represents an alkali metal atom, in particular a sodium or potassium atom, or an ammonium or alkylammonium group.

Processes 1 and 2 are both conveniently conducted at normal pressure and at a temperature of from 0° to 80° C., preferably 20° to 50° C. in the presence of solvents and/or diluents which are inert towards the reactants.

Examples of suitable solvents or diluents are: ether and ethereal compounds, such as diethyl ether, dipropyl ether, dioxan and tetrahydrofuran; amides, such as N,N-dialkylated carboxy amides; aliphatic, aromatic, and halogenated hydrocarbons, in particular benzene, toluene, xylene, chloroform and chlorobenzene; and nitriles, such as acetonitrile.

Suitable bases for use in the reaction 1 include the hydroxides and carbonates of the alkali and alkaline earth metals, in particular sodium and potassium carbonate.

The starting materials for use in the above processes are known [see for example J. Org. Chem. 30, 3217, (1965)] or may be prepared in a manner analogous to that used for preparing the known compounds.

The compounds of the formula I are suitable for combating a variety of pests, in particular pests of the class Insecta and of the order Acarina and are for example especially useful for combating Insects and Acarids which cause damage to plants, e.g. agriculture and horticultural crops, or to productive livestock.

Thus the compounds of the formula I may be employed against the eggs, larvae, nymphs, pupae or adults of insects of the families: Acrididae, Blattidae, Gryllidae, Gryllotalpidae, Tettigoniidae, Cimicidae, Pyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culcidae, Tipulidae, Stomoxydae, Muscidae, Clliphoridae, Trypetidae, Pulicidae, as well as against mites, spider mites and/or ticks of the families: Ixodidae, Argasidae, Tetranychidae and Dermanyssidae.

In the above connection particular mention may be made of the utility of the subject compounds in combating insects of the species Leptinotarsa decemlineata, *Spodoptera littoralis, Heliothis virescens, Myzus persicae* and *Chilo suppressalis* in, for example, vegetable, fruit, rice and cotton crops as well as in combating houshold and hygiene insect pests such as those of the species *Musca domestica* and *Aedes aegypti.*

The insecticidal or acaricidal action of the subject compounds can be substantially broadened and adapted to given circumstances by the addition of other insecticides and/or acaricides. Examples of suitable additives are: organic phosphorus compounds, derivatives of nitrophenols, formamidines, ureas, carbamates and chlorinated hydrocarbons.

The compounds of the formula I may be used as pure active substance or in composition form together with suitable carriers and/or additives. Suitable carriers and additives can be solid or liquid and correspond to the substances conventionally used in formulation technology, for example natural or regenerated substances, solvents, dispersants, wetting agents, adhesives, thickeners, binders and/or fertilisers.

For application, the compounds of the formula I may be processed to dusts, emulsion concentrates, granules, dispersions, sprays, to solutions, or suspensions, in the conventional formulation which is commonly employed in application technology.

Pesticidal compositions may for example be manufactured in known manner by intimately mixing or grinding the compounds of the formula I with the suitable carriers, with or without the addition of dispersants or solvents which are inert to the active substances.

The active substances may take, and be used in, the following forms: Solid forms:

Dusts, tracking agents and granules (coated granules, impregnated granules and homogeneous granules). Liquid forms:

(a) active substances which are dispersible in water: wettable powders, pastes and emulsions;
(b) solutions.

The content of active substance in the above described compositions is generally between 0.1% and 95%.

The active substances of the formula I can, for example, be formulated as follows (throughout the present specification all parts and percentages are by weight):

Dusts

The following substances are used to manufacture (a) a 5% and (b) a 2% dust:
(a) 5 parts of active substance,
 95 parts of talc;
(b) 2 parts of active substance,
 1 part of highly disperse silicic acid,
 97 parts of talc.

The active substances are mixed with the carriers and ground.

Granules

The following substances are used to produce 5% granules:
 5 parts of active substance,
 0.25 parts of epichlorohydrin,
 0.25 parts of cetyl polyglycol ether,
 3.50 parts of polyethylene glycol,
 91 parts of kaolin (particle size 0.3–0.8 mm).

The active substance is mixed with epichlorohydrin and dissolved with 6 parts of acetone; the polyethylene glycol and cetyl polyglycol ether are then added. The resultant solution is sprayed on kaolin, and the acetone is subsequently evaporated in vacuo.

Wettable powder:

The following constituents are used for the preparation of (a) a 40%, (b) and (c) a 25%, and (d) a 10% wettable powder:
(a) 40 parts of active substance,
 5 parts of sodium lignin sulphonate,
 1 part of sodium dibutyl-naphthalene sulphonate,
 54 parts of silicic acid.
(b) 25 parts of active substance,
 4.5 parts of calcium lignin sulphonate,
 1.9 parts of Champagne chalk/hydroxyethyl cellulose mixture (1:1),
 1.5 parts of sodium dibutyl naphthalene sulphonate,
 19.5 parts of silicic acid,
 19.5 parts of Champagne chalk,
 28.1 parts of kaolin,
(c) 25 parts of active substance,
 2.5 parts of isooctylphenoxy-polyoxyethyleneethanol,
 1.7 parts of Champagne chalk/hydroxyethyl cellulose mixture (1:1),
 8.3 parts of sodium aluminum silicate,
 16.5 parts of kieselguhr,
 46 parts of kaolin,
(d) 10 parts of active substance,
 3 parts of a mixture of the sodium salts of saturated fatty alcohol sulphates,
 5 parts of naphthalenesulphonic acid/formaldehyde condensate,
 82 parts of kaolin.

The active substances are homogeneously mixed, in suitable mixers, with the additives, the mixture being then ground in the appropriate mills and rollers. Wettable powders are obtained which can be diluted with water to give suspensions of the desired concentration.

Emulsifiable concentrates:

The following substances are used to produce (a) a 10%, (b) a 25%, and (c) a 50% emulsifiable concentrate:
(a) 10 parts of active substance,
 3.4 parts of epoxidised vegetable oil,
 3.4 parts of a combination emulsifier consisting of fatty alcohol polyglycol ether and alkylarylsulphonate calcium salt,
 40 parts of dimethyl formamide,
 43.2 parts of xylene;
(b) 25 parts of active substance,
 2.5 parts of epoxidised vegetable oil,
 10 parts of alkylarylsulphonate/fatty alcohol polyglycol ether mixture,
 5 parts of dimethyl formamide,
 57.5 parts of xylene;
(c) 50 parts of active substance,
 4.2 parts of tributylphenol-polyglycol ether,
 5.8 parts of calcium-dodecylbenzenesulphonate,
 20 parts of cyclohexanone,
 20 parts of xylene.

By diluting these concentrates with water it is possible to obtain emulsions of the required concentration.

Spray:

The following ingredients are used to prepare (a) a 5% spray, and (b) a 95% spray:
(a) 5 parts of active substance,
 1 part of epichlorohydrin,
 94 parts of ligroin (boiling range 160°–190° C.);
(b) 95 parts of active substance,
 5 parts of epichlorohydrin.

The invention is further illustrated by the following Examples:

EXAMPLE 1

Preparation of O-ethyl-S-n-propyl-O-[3-(1,3-dithiolan-2-yl)-phenyl]-thiolophosphoric acid ester 8.4 g of triethylamine were added to 15.9 g of 3-(1,3-dithiolan-2-yl)-phenol dissolved in 120 ml of benzene. 16.3 g of O-ethyl-S-n-propyl-chloro-thiolophosphoric acid ester were then added dropwise with stirring to the obtained solution.

After a further 12 hours continuous stirring at room temperature the reaction mixture was washed first with water, then with a 3% sodium carbonate solution and finally again with water. The solution was next dried over anhydrous sodium sulfate, the benzene distilled off and the obtained product dried under high-vacuum. There was thus obtained the product of the formula

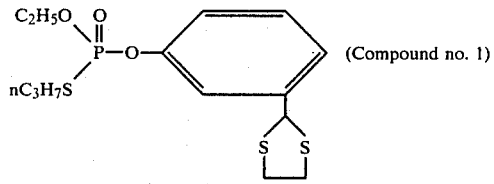

(Compound no. 1)

as a lightbrown oil having a refractive index of $n_D^{20}$: 1.5783.

The following compounds may be obtained analogously:

| Compound No. | Structure | Physical data |
|---|---|---|
| 2 | $C_2H_5O$, $nC_3H_7S$ >P(=O)−O−(phenyl)−CH(S−S ring) | $n_D^{22}$: 1.5791 |
| 3 | $C_2H_5O$, $nC_3H_7S$ >P(=O)−O−(phenyl)−CH(S−S ring)−$C_2H_5$ | $n_D^{20}$: 1.5254 |
| 4 | $C_2H_5O$, $nC_3H_7S$ >P(=O)−O−(phenyl)−CH(S−S ring with CH$_3$) | $n_D^{20}$: 1.5698 |
| 5 | $C_2H_5O$, $nC_3H_7S$ >P(=O)−O−(phenyl)−CH(S−S 6-ring) | $n_D^{20}$: 1.5870 |
| 6 | $C_2H_5O$, $nC_3H_7S$ >P(=O)−O−(phenyl)−C(CH$_3$)(S−S ring) | $n_D^{20}$: 1.5705 |
| 7 | $C_2H_5O$, $nC_3H_7S$ >P(=S)−O−(phenyl)−CH(S−S ring) | $n_D^{20}$: 1.5985 |
| 8 | $C_2H_5O$, $nC_3H_7S$ >P(=O)−O−(phenyl)−CH(O−S ring) | $n_D^{20}$: 1.5542 |
| 9 | $C_2H_5O$, $nC_3H_7S$ >P(=S)−O−(phenyl)−CH(O−S ring) | Oil |

In the following biological examples the compound of the formula

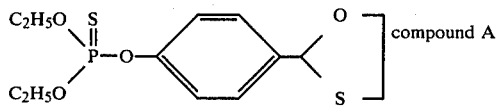

compound A which is a known compound described in U.S. Pat. No. 3,247,223 is employed for comparative purposes.

EXAMPLE 2

Activity against Leptinotarsa decemlineata larvae

Test method

Each of the test compounds (formulated as a 25% wettable powder) was made up into an emulsion containing 1000 ppm. of the compound. Potato plants in the 4- to 5- leaf stage were then immersed in the prepared emulsions, one plant being employed per emulsion. After removal and drying of the plants, each was infested with five larvae of the species *Leptinotarsa decemlineata* at the L3 instar and covered with a plastic cylinder capped by wire netting to avoid escape of the larvae from the plant.

The percentage mortality amongst the larvae on each plant was estimated two days and three days later.

Test results:

The compounds according to example 1 exhibited a positive action against larvae of the species Leptinotarsa decemlineata in this test. Thus employing compounds 7, 8 and 9 according to example 1, 100% mortality was achieved in the above test after two days. Employing the comparative compound A there was zero mortality after three days.

EXAMPLE 3

Activity against *Spodoptera littoralis* larvae (I):

Test method

The method of Example 2 was repeated exactly but using cotton plants and 5 larvae of the species *Spodoptera littoralis* instead of potato plants and larvae of the species *Leptinotarsa decemlineata*. The Spodoptera littoralis larvae employed were at the L3 instar.

Test results:

The compounds according to example 1 showed a positive action in this test. Thus employing compounds 7, 8 and 9 according to example 1, 100% mortality was achieved in this test after two days. Employing the comparative compound A there was zero mortality after three days.

EXAMPLE 4

Activity against *Spodoptera littoralis* larvae (II):

Test method

Cotton plants were sprayed with a 0.05% aqueous emulsion of the test compound said compound having been prepared from a 10% emulsifiable concentrate. After the coating had dried the plants were populated with larvae of the species *Spodoptera littoralis* at the 3rd instar. Two plants were employed per test compound and an evaluation of the % mortality achieved was conducted at intervals of 2, 4, 24 and 48 hours after population. The test was carried out at a temperature of 24° C. and at 60% relative humidity.

Test results:

The compounds according to example 1 showed a positive action against larvae of the species *Spodoptera littoralis* in the above test. For the compounds 7, 8 and 9 according to example 1 and the comparative compound A the following results were achieved:

| Compound | % mortality after ..... hours | | | |
|---|---|---|---|---|
| | 2 | 4 | 24 | 48 |
| 7 | 90 | 100 | — | — |
| 8 | 100 | — | — | — |
| 9 | 100 | — | — | — |
| A | 0 | 0 | 0 | 0 |

EXAMPLE 5

Activity against *Heliothis virescens* larvae

Test method

The method of example 1 was repeated exactly but using cotton plants and larvae of the species *Heliothis virescens* (3rd instar) instead of potato plants and larvae of the species *Spodoptera littoralis*.

Test results:

The compounds according to example 1 showed a positive action in this test against larvae of the species *Heliothis virescens*. The following results were for example obtained with the compounds 7, 8 and 9 according to example 1 and with the comparative compound

| Compound | % mortality after ..... hours | | | |
|---|---|---|---|---|
| | 2 | 4 | 24 | 48 |
| 7 | 0 | 40 | 100 | — |
| 8 | 30 | 80 | 100 | — |
| 9 | 0 | 40 | 90 | 100 |
| A | 0 | 0 | 0 | 0 |

EXAMPLE 6

Activity against *Musca domestica*

Test method

From each compound under test two acetonic solutions were made up, one containing 5000 ppm. and the other 1000 ppm. test compound. Sixteen petri dishes were then taken each measuring 9 cm in diameter. One ml quantities were then pipetted from the acetonic solutions into the petri dishes, two perti dishes being employed per solution. When the acetone had evaporated 5 lightly anaesthatised insects of the species *Musca domestica* were introduced into each petri dish. The test was deemed to have commenced when 50% of the flies in the dishes had recovered from narcosis, and the condition of the flies was noted at intervals of ¼, ½, 1, 2, 4 and 8 hours thereafter. The minimum time was noted for each test compound at each concentration after which 100% mortality was achieved.

Test results:

The compounds according to example 1 showed a good action against insects of the species *Musca domestica* in the above test. The following results were achieved with compounds 7, 8 and 9 according to example 1 and with the comparative compound A.

| TEST COMPOUND CONCENTRATION | MINIMUM TIME REQUIRED FOR 100% MORTALITY | | | |
|---|---|---|---|---|
| | COMPOUND 7 | COMPOUND 8 | COMPOUND 9 | COMPOUND A |
| 5000 ppm | 1 hr | ¼ hr | 1 hr | 100% mortality not achieved after 8 hrs |
| 1000 ppm | 2 hrs | 1 hr | 1 hr | 100% mortality not achieved after 8 hrs |

EXAMPLE 7

Activity against *Myzus persicae*

Test method

Before commencement of the test beanplants (*Vicia faba*) were infested with approximately 200 individuals of the species *Myzus persicae*. Twentyfour hours later the plants were sprayed until dripping with an aqueous solution containing 200 ppm. of the compound under test, said solution having been obtained from a 25% wettable powder. The spray was directed from a distance of approx. 30 cm directly onto the infested leaves. Two plants were employed per test compound and the % mortality achieved was estimated two days after spraying.

Test results:

The compounds according to example 1 showed a positive action in the above test against insects of the species *Myzus persicae*. Thus compounds 7, 8 and 9 according to example 1 all gave 100% kill after two days. In contrast a zero percent kill was achieved using the comparative compound A.

EXAMPLE 8

Action against *Chilo suppressalis* larvae

Rice seedlings of the variety Caloro were reared in plastic pots (6 seedlings per pot) so that their roots became matted to a disc. The roots were then immersed in a 0.08% solution of active substance and allowed to drip off. Then each pot was polulated with 5 *Chilo suppressalis* larvae in the $L_2$-stage and the treated plants were subsequently replaced in the pots on top of the larvae.

Evaluation of mortality was made after 5 days and the test was carried out at 24° C. and 70% relative humidity. The compounds according to example 1 acted well in this test against *Chilo suppressalis* larvae.

EXAMPLE 9

Action against adults and larvae of the species *Tetranychus urticae* (OP-sensitive) and *Tetranychus cinnabarius* (OP-resistant)

The primary leaves of *Phaseolus vulgaris* plants were infected with an infested piece of leaf from a massculture of *Tetranychus urticae* (OP-sensitive) and/or *Tetranychus cinnabarius* (OP-resistant) 16 hours before the test for acaricidal action. (The resistance refers to the tolerance to diazinone). The mobile stages which had migrated to the plants were sprayed from a chromatographic atomiser with an emulsified test preparation containing 400 ppm of active substance. The number of living and dead adults and larvae (all mobile stages) was evaluated under a stereoscopic microscope after 24 hours and again after 7 days.

One plant was used per test substance and per test species. During the test run, the plants stored in greenhouse compartments at 25° C.

In this test, the compounds of Example 1 acted against adults and larvae of the species *Tetranychus urticae* and *Tetranychus cinnabarius*.

EXAMPLE 10

Action against *Rhipicephalus bursa* and *Boophilus microplus* (OP-sensitive and OP-resistant)

Five adults or approx. 50 larvae of the species *Rhipicephalus bursa*, or 20 OP-sensitive or 20 OP-resistant larvae of the species *Boophilus microplus*, were counted into each of a number of test tubes and immersed for 1 to 2 minutes in 2 ml of an aqueous emulsion containing 100, 50, 10, or 1 ppm of test substance. Each test tube was then sealed with a cotton wool plug and placed on its head to enable the cotton wool to absorb excess active substance emulsion.

The mortality rate of the adults was evaluated after 2 weeks and that of the larvae of both species after 3 days. Each test was repeated twice (development stage or tolerance/species/active substance concentration).

In these tests, the compounds of Example 1 acted against adults and larvae of *Rhipicephalus bursa* and on OP-sensitive and OP-resistant larvae of *Boophilus microplus*.

We claim:

1. A compound of the formula

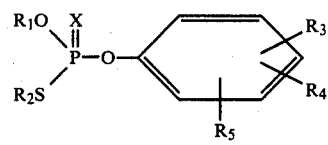

wherein
R$_1$ represents methyl or ethyl,
R$_2$ represents n-propyl, i-butyl or sec.-butyl,
R$_3$ and R$_4$ each represents hydrogen, chlorine, bromine, methyl or ethyl,
R$_5$ represents a group of the formula

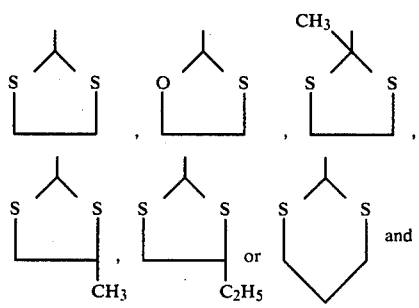

and
X represents oxygen or sulfur.

2. A compound according to claim 1, wherein
R$_2$ represents n-propyl or sec.-butyl and
X represents oxygen.

3. A compound according to claim 2 of the formula

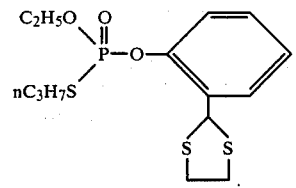

4. A compound according to claim 2 of the formula

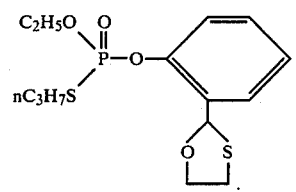

5. A compound according to claim 2 of the formula

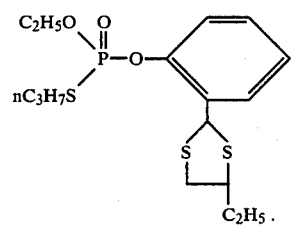

6. A compound according to claim 2 of the formula

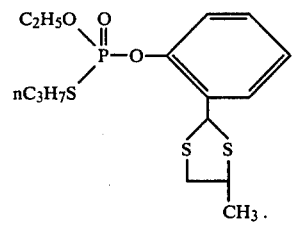

7. A compound according to claim 2 of the formula

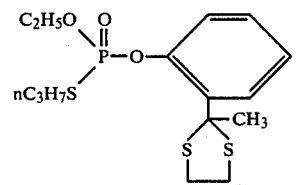

8. An insecticidal and acaricidal composition comprising (1) an insecticidally or acaricidally effective amount of a compound according to claim 1 and (2) a carrier.

9. A composition according to claim 8 in which, in the compound, $R_2$ represents n-propyl or sec.butyl and X represents oxygen.

10. A method for combating insects and acarids which comprises applying thereto an insecticidally or acaricidally effective amount of a compound according to claim 1.

11. A method according to claim 10 in which, in the compound, $R_2$ represents n-propyl or sec.butyl and X represents oxygen.

12. The method according to claim 11 in which the compound is O-ethyl-S-n-propyl-O-[2-(1,3-dithiolan-2-yl)-phenyl]-thiolophosphoric acid ester.

13. The method according to claim 11 in which the compound is O-ethyl-S-n-propyl-O-[2-(1,3-oxathiolan-2-yl)-phenyl]-thiolophosphoric acid ester.

14. The method according to claim 11 in which the compound is O-ethyl-S-n-propyl-O-[2-(4-ethyl-1,3-dithiolan-2-yl)-phenyl]-thiolophosphoric acid ester.

15. The method according to claim 11 in which the compound is O-ethyl-S-n-propyl-O-[2-(4-methyl-1,3-dithiolan-2-yl)-phenyl]-thiolophosphoric acid ester.

16. The method according to claim 11 in which the compound is O-ethyl-S-n-propyl-O-[2-(2-methyl-1,3-dithiolan-2-yl)-phenyl]-thiolophosphoric acid ester.

* * * * *